US007874997B2

(12) United States Patent
Jaccard (10) Patent No.: US 7,874,997 B2
(45) Date of Patent: Jan. 25, 2011

(54) MEDICAL PRODUCT, ALSO FOR SPORTS USE, AND RELATIVE MANUFACTURING METHOD

(75) Inventor: Jean-Patrick Jaccard, Caslano (CH)

(73) Assignee: Sports & Supports Limited, Dublin (IE)

(*) Notice: Subject to any disclaimer, the term of this patent is extended or adjusted under 35 U.S.C. 154(b) by 150 days.

(21) Appl. No.: 11/663,195

(22) PCT Filed: Aug. 8, 2005

(86) PCT No.: PCT/EP2005/008597

§ 371 (c)(1),
(2), (4) Date: Mar. 19, 2007

(87) PCT Pub. No.: WO2006/032325

PCT Pub. Date: Mar. 30, 2006

(65) Prior Publication Data

US 2008/0119771 A1    May 22, 2008

(30) Foreign Application Priority Data

Sep. 22, 2004  (IT) .......................... MI2004A1810

(51) Int. Cl.
 *A61F 5/00* (2006.01)
 *A61F 5/37* (2006.01)
 *A41D 13/08* (2006.01)
(52) U.S. Cl. .................... 602/27; 602/21; 128/846; 2/16

(58) Field of Classification Search .................. 602/16, 602/18, 23, 26, 27, 24, 19, 5, 20, 21; 128/846; 24/715.4; 2/170, 162, 16, 163, 18–19, 22, 2/311, 316, 320, 321, 338, 910, 911, 920
See application file for complete search history.

(56) References Cited

U.S. PATENT DOCUMENTS

| | | | |
|---|---|---|---|
| 2,206,404 A * | 7/1940 | Jones | 602/21 |
| 4,176,839 A | 12/1979 | Pinkus | |
| 4,825,856 A * | 5/1989 | Nelson | 602/27 |
| 5,160,314 A * | 11/1992 | Peters | 602/21 |
| 5,221,252 A * | 6/1993 | Caprio et al. | 602/63 |
| 5,695,452 A | 12/1997 | Grim et al. | |
| 5,769,804 A * | 6/1998 | Harris et al. | 602/21 |
| 5,865,777 A | 2/1999 | Detty et al. | |
| 6,042,557 A | 3/2000 | Ferguson et al. | |
| 6,488,643 B1 * | 12/2002 | Tumey et al. | 602/13 |
| 6,572,600 B1 | 6/2003 | Roe et al. | |
| 6,893,410 B1 * | 5/2005 | Hely | 602/21 |
| 2005/0142334 A1* | 6/2005 | Mikata et al. | 428/190 |

FOREIGN PATENT DOCUMENTS

EP    368583 A1 *  5/1990

* cited by examiner

*Primary Examiner*—Patricia M Bianco
*Assistant Examiner*—Ophelia Hawthorne
(74) *Attorney, Agent, or Firm*—Young & Thompson (57) ABSTRACT

A health product for sports use, in particular a joint support includes a main strap (5; 105; 205; 305) destined to surround the part of the body to be supported. The main strap includes: a bottom layer (2) destined to come into contact with the skin of the wearer, an intermediate layer of padding (3), and a top layer (4) destined to face outward. The main strap is obtained by die-punching and moulding along the peripheral edge.

10 Claims, 10 Drawing Sheets

MEDICAL PRODUCT, ALSO FOR SPORTS USE, AND RELATIVE MANUFACTURING METHOD

FIELD OF THE INVENTION

The present invention refers to the field of products for medical or orthopaedic use for rehabilitation and prevention of injuries. It refers in particular to joint supports, such as splints, wrist braces, straps, thigh braces, ankle braces and the like. The present invention also extends to protective products for sports use, for sports in which there is a high stress on the joint, which must be protected.

BACKGROUND OF THE INVENTION

Various types of joint support are widely available on the market, such as, for example:
  thumb splints: indicated for dislocations, strains and fractures of the thumb or also for lesions of the thumb ligament in sports injuries;
  wrist splints: indicated for dislocations and sprains of the wrist and for carpal tunnel syndrome;
  wrist braces: indicated for dislocations, slight lesions and small injuries of the wrist;
  epicondylitis straps: indicated for radial and/or medial epicondylitis and tendinitis of the elbow;
  corsets: indicated for mild spinal injuries;
  thigh braces: indicated for contractures, pulls and sprains of the quadriceps muscle;
  knee braces: indicated for injuries of the knee joints;
  ankle braces: particularly indicated in control of ankle eversion and inversion of the ankle; and
  elastic ankle supports: indicated after mild tibio-tarsal injuries.

These joint supports generally include a main strap designed to surround the part of the body in which the joint to be protected is situated. This main strap is made of multilayer material comprising:
  a bottom layer, of anallegic material, destined to come into contact with the skin of the wearer,
  a top layer of material suitable for Velcro-type fastening (mutually engageable hooks and loops), and
  an intermediate layer of padding consisting of a soft, breathable material.

The bottom and top layers are edged and sewn along the whole perimeter of the main band so as to enclose the padding on their inside.

Pockets are sewn onto the top layer possibly to contain metal stiffening plates.

At one end of the main band a plurality of eyelets are created by cutting. At the other end of the main band a plurality of laces are sewn which are inserted into the respective eyelets so as to close the strap in a tubular shape.

Velcro type fastening elements consisting of a plurality of hooks able to engage with the hooked wires of the upper layer of the main strap are sewn to the free end of the main strap.

In this manner, by pulling the laces, the strap is suitably tightened around the part of the body on which it is applied and exerts an adequate pressure on the joints which are protected and immobilised. Once the desired pressure has been reached, the Velcro fastening element is applied to the top layer of the strap to keep it closed and suitably tightened.

The production procedure for these products is somewhat long, complex and costly because of the various operations of edging and sewing to which both the strap and the laces are subjected.

Furthermore, the product obtained presents some drawbacks. In fact it often happens that the laces come into direct contact with the skin, resulting in skin irritations due to the production material of the laces. As a result a further additional element must be provided in the support, in the form of a protective sock, which is sewn to the main strap so as to be interposed between the laces and the wearer's skin.

Furthermore, in the joint supports of the prior art, it is necessary to design the length of the laces to ensure that, when the support is suitably tightened, the Velcro fastening element is situated on the strap and not on the laces on which it has no grip. As a result, joint supports of the prior art are not very versatile and do not adapt well to the different sizes and shapes of the parts of the body to be protected.

SUMMARY OF THE INVENTION

The object of the present invention is to overcome the drawbacks of the prior art, providing a medical product also for sports use that is versatile, practical, inexpensive and easy to make.

These objects are achieved according to the invention with the article and the production method whose characteristics are listed in appended independent claims 1 and 12, respectively.

Advantageous embodiments of the invention are apparent from the dependent claims.

The medical product, also for sports use, according to the invention, comprises a main strap designed to surround the part of the body to be supported. The main strap comprises: a bottom layer destined to come into contact with the wearer's skin, an intermediate layer of padding, and a top layer destined to face outwards. The main strap is obtained from a multilayer sheet obtained by bonding of a plurality of layers of different materials. The multilayer sheet is die-punched and moulded or welded or thermoformed along its outer edge.

As an alternative to moulding, welding or heat-forming, the multi-layer sheet can be die-punched cold along its outer edge or part of its outer edge.

In this manner the operations of edging and sewing of the outer edge of the strap to contain the padding between the top layer and the bottom layer are eliminated.

The tightening laces can advantageously be made in a single piece with said main strap during this stage of die-punching and moulding. Therefore, the tightening laces also have the advantage of having an undersurface of anallergic material and a top surface of material such as to allow Velcro type fastening.

BRIEF DESCRIPTION OF THE DRAWINGS

Further characteristics of the invention will be made clearer by the detailed description that follows, referring to purely exemplary and therefore non-limiting embodiments thereof, illustrated in the appended drawings, in which.

DETAILED DESCRIPTION OF EMBODIMENTS

Figure 3:
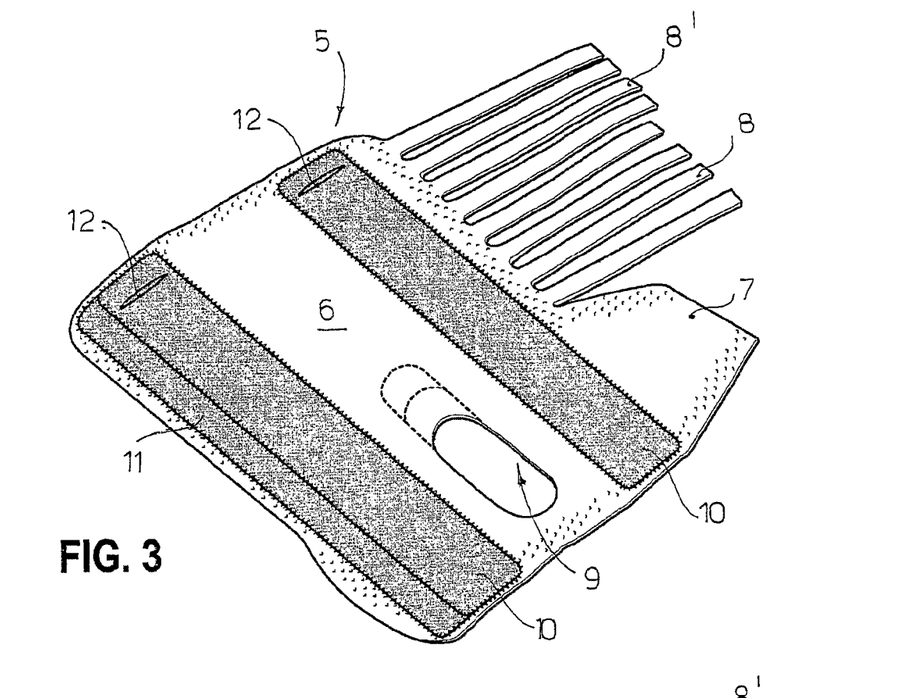
Figure 4:
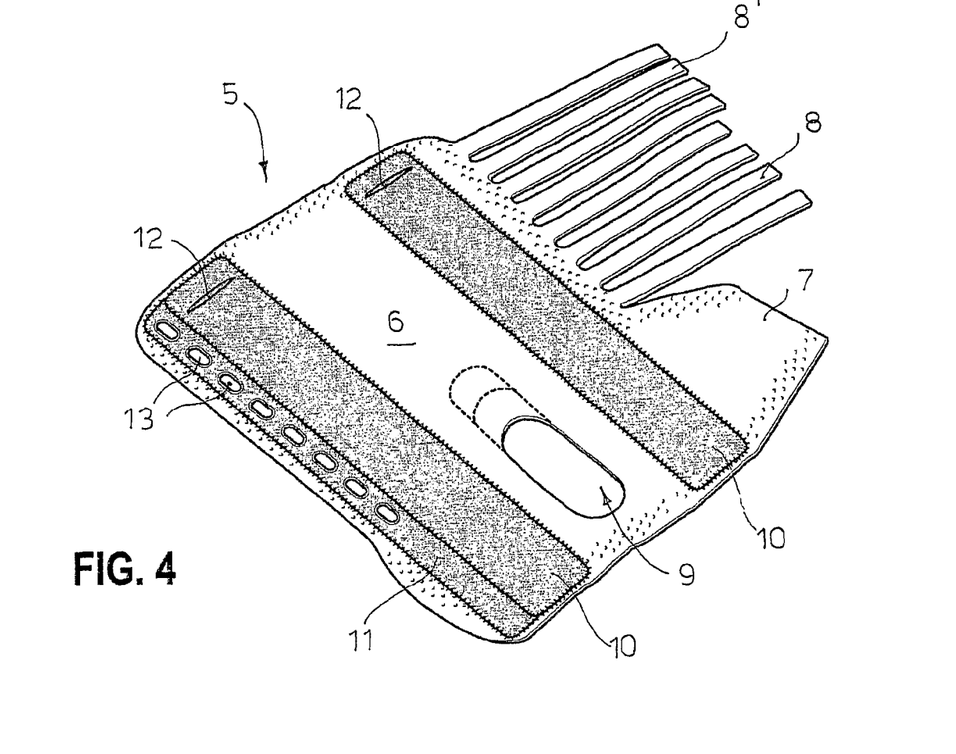
Figure 5:
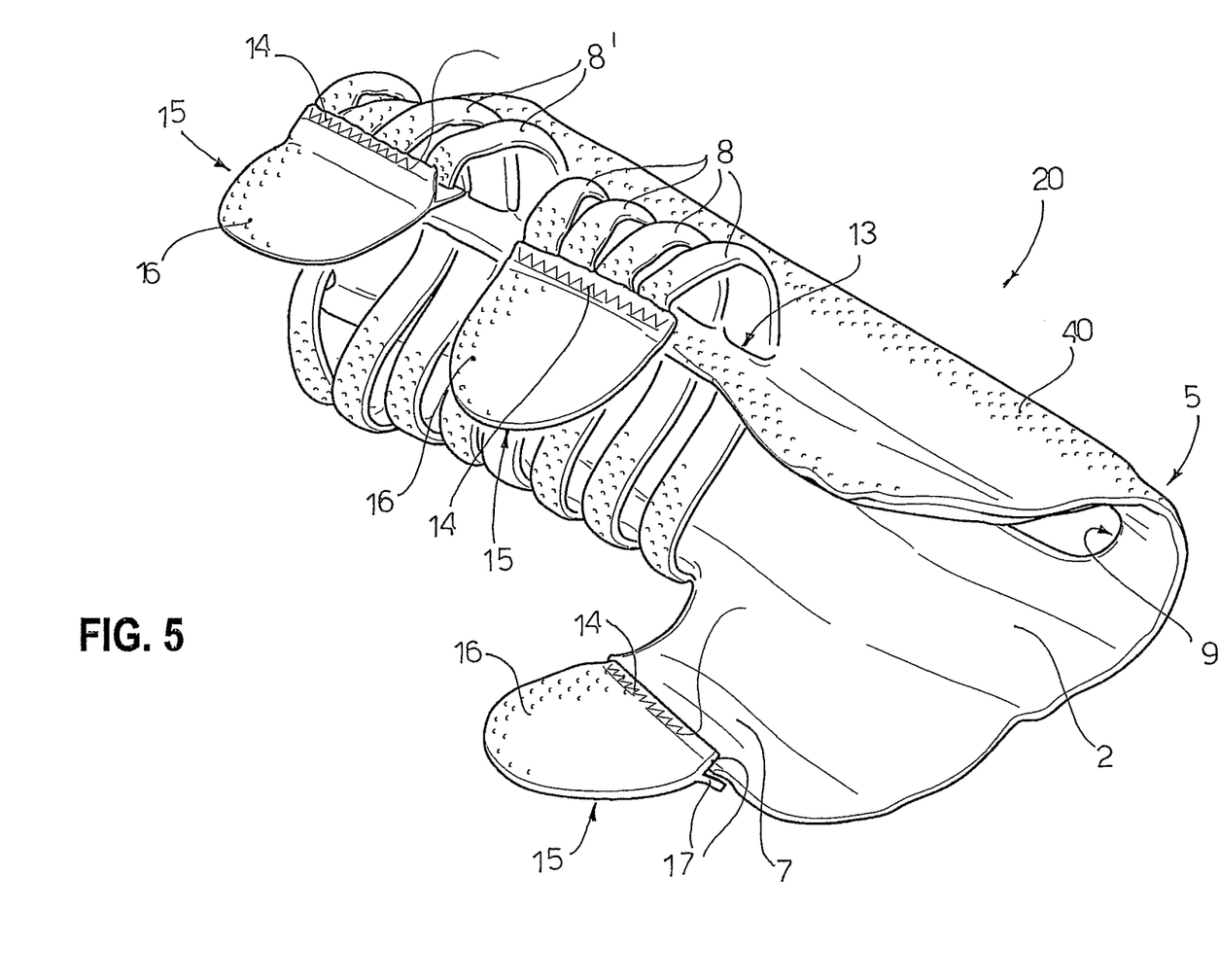
FIG. 5 is a perspective view illustrating the last stage of production of the wrist splint according to the invention.

With reference for now to FIGS. 1-8, a first embodiment of a product according to the invention, in the form of a wrist splint, illustrated as a whole in FIG. 5 and denoted by reference numeral 20, will now be described.

Figure 1:
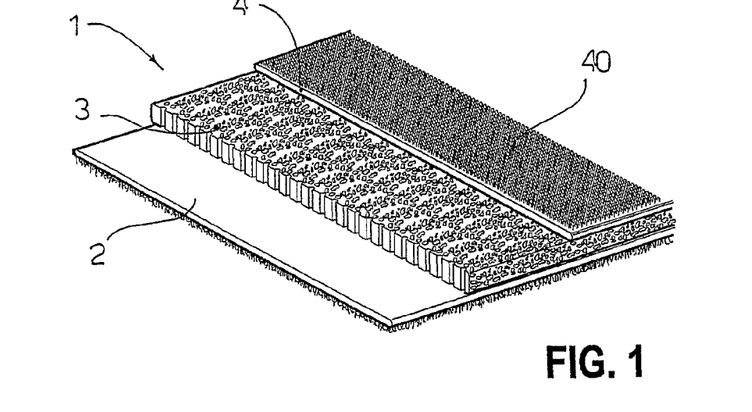
FIG. 1 is a partially broken off perspective view in cross section, illustrating a multi-layer sheet used to make products according to the invention.

Production of the wrist splint 20 and of all the other products according to the invention starts from a flat, multi-layer sheet 1, as illustrated in FIG. 1, which forms the basic element for production of the products according to the invention. The multilayer sheet 1 is made up of several layers of material coupled to one another. Flame bonding is preferably used. The multilayer sheet 1 comprises:

a bottom layer 2 destined to come into contact with the wearer's skin, an intermediate layer of padding 3, and a top layer 4 destined to face outward.

The bottom layer 2, being in contact with the skin, must be made of anallergic material, such as cotton fabric.

The intermediate layer 3 must be made of a cushioning, breathable material, such as, for example, open-cell foamed plastic material such as polyurethane. (PU).

The top layer 4 must have a top surface 40 suitable for a Velcro-type coupling. Therefore, the top surface 40 of the top layer 4 has a plurality of loops able to couple in a fastening relationship with a plurality of matching hooks of a Velcro-type fastening element, as will be described hereunder.

For this purpose the top layer 4 can be made of nylon fabric suitably treated so as to obtain an upper surface 40 with a plurality of loops.

Flame bonding of the multilayer sheet 1 takes place by feeding from two respective rolls the bottom layer 2 and the intermediate layer 3, which is made to pass near a flame which heats it on the surface facing the bottom layer 2 to allow bonding thereof. Then, the two layers 2 and 3 are made to pass through a calender which performs bonding. Subsequently, the outside of the intermediate layer 3 is heated by means of a flame and bonded by means of a calender with the top layer 4 fed from a roll.

The intermediate layer 3, made of PU, allows good adhesion with the bottom layer 2 and the top layer 4, by means of flame bonding. Flame bonding is an example of the types of coupling that can be made between materials. Alternatively there are other methods such as spread or sprayed glue, hot glue, etc.

Figure 2:
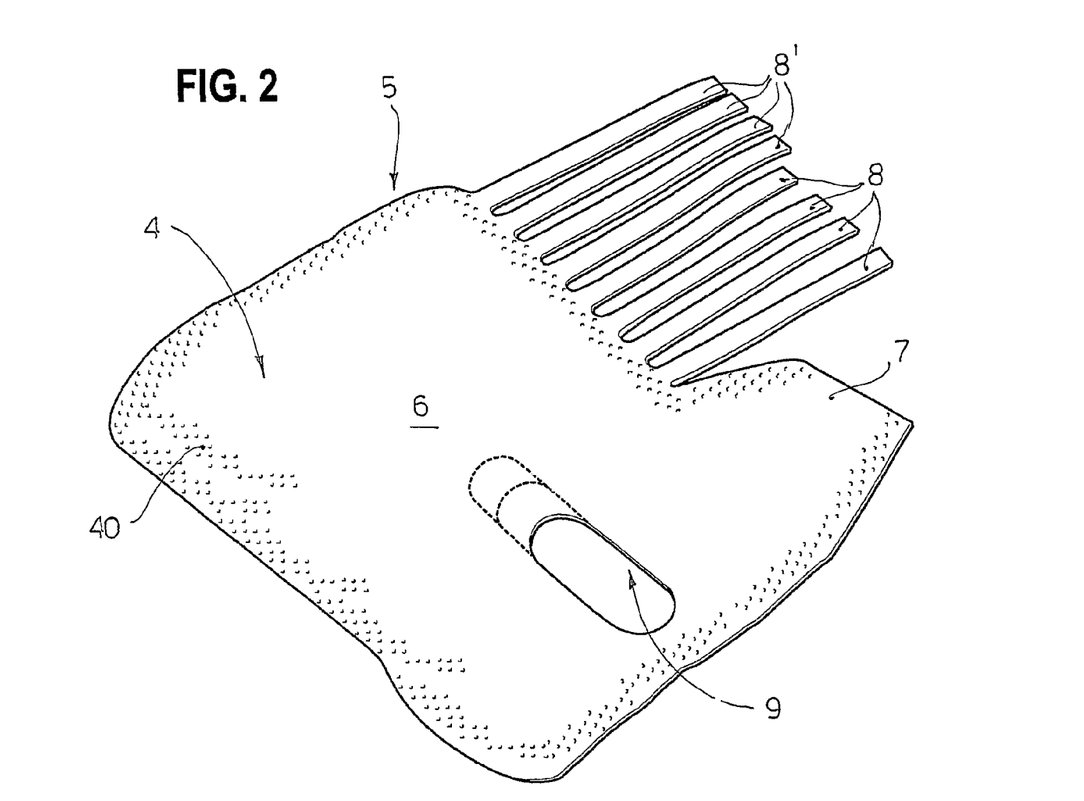
FIGS. 2-4 are three top plan views illustrating a strap spread out in three consecutive stages of processing for production of a product according to a first embodiment of the invention which provides a wrist splint.

The multi-layer sheet 1, having a substantially rectangular shape, is fed through a die-punching and pressure moulding machine. Then, the multilayer sheet 1 is compressed between two mould halves which simultaneously perform die-punching and moulding along the pre-established perimeter, so as to obtain a strap 5, as shown in FIG. 2.

The strap 5 comprises a substantially rectangular central portion 6. The longer sides of the central portion 6 follow the longitudinal direction of the strap 5; on the contrary, the shorter sides of the central portion 6 follow the cross direction of the strap 5.

A trapezoidal side band 7 and a plurality of rectangular strips or laces 8, 8', having a greater length and a smaller width with respect to the side band 7, protrude from one side of the central portion 6. The side band 7 and the laces 8, 8' extend in the crosswise direction of the strap 5.

By way of example, the laces 8, 8' are eight in number and the first four laces 8 starting from the side band 7 have a slightly shorter length than the other four laces 8'.

In the central portion 6, in a central position and level with the side band 7, a slot 9 is formed by die-punching and is of such a size as to allow insertion of the thumb of a hand. The slot 9 extends in the lengthwise direction of the strap 5.

It must be considered that pressure moulding is performed all along the outer peripheral edge of the central portion 6, the side band 7 and the laces 8, 8' and also all along the peripheral edge of the slot 9. Hot moulding is preferably performed, so as to obtain heat welding or thermoforming of the intermediate layer 3 to the bottom and top layers 2 and 4, along the peripheral edge. For this purpose the intermediate layer 3 must be of heat-weldable material, such as polyurethane for example.

Alternatively, instead of heat welding, ultrasound welding using a mould half vibrating at the frequency of ultrasound can be used.

Alternatively, for reasons of cost, hot moulding or ultrasound moulding of the peripheral edge of the multilayer sheet 1 can be avoided, using only cold die-punching.

As shown in FIG. 3, on the central portion 6 of the strap 5, on one side and the other with respect to the slot 9, two longitudinal pockets 10, provided with respective openings 12 for insertion of metal plates for stiffening of the structure, are applied by sewing.

Again on the central portion 6, at the side of one pocket 10, near the opposite side to that in which the laces 8, 8' are situated, a longitudinal reinforcing strip 11 is sewn.

The pockets 10 and the reinforcing strip 11 are preferably made of the same material as the top layer 4, or in any case of a material suitable to allow Velcro-type fastening.

As shown in FIG. 4, a plurality of eyelets 13 are made in the reinforcing strip by die-punching, in a number equal to that of the laces 8, 8' and in a position coinciding with said laces 8, 8', in a crosswise direction. The eyelets 13 are wide enough to accommodate the respective laces 8, 8'.

As shown in FIG. 5, the laces 8, 8' are inserted in the respective eyelets 13 and pulled so that the strap 5 takes on a substantially tubular shape.

At this point, three Velcro-type fastening elements 15 are applied to the strap 5, by means of sewing 14. To be precise, a first fastening element 15 is applied to the free end of the group of four longer laces 8', a second fastening element 15 is applied to the free end of the group of four shorter laces 8 and a third fastening element 15 is applied to the end of the side band 7.

Each fastening element 15 is shaped like a substantially semi-elliptical patch of such a size as to be able to be gripped easily by the wearer. The fastening element 15 has two end flaps 17, disposed in a substantially V-shaped configuration, to be sewn to the ends of the laces 8, 8' and of the side band 7. On one surface of the fastening elements 15 there are provided a plurality of hooks 16 able to engage, in a fastening relationship, with the loops 40 disposed on the top surface of the strap 5 and of the laces 8, 8'.

In this manner, the wrist splint 20, illustrated in FIG. 5, is obtained, ready to be worn on the wrist of a wearer.

Figure 6:
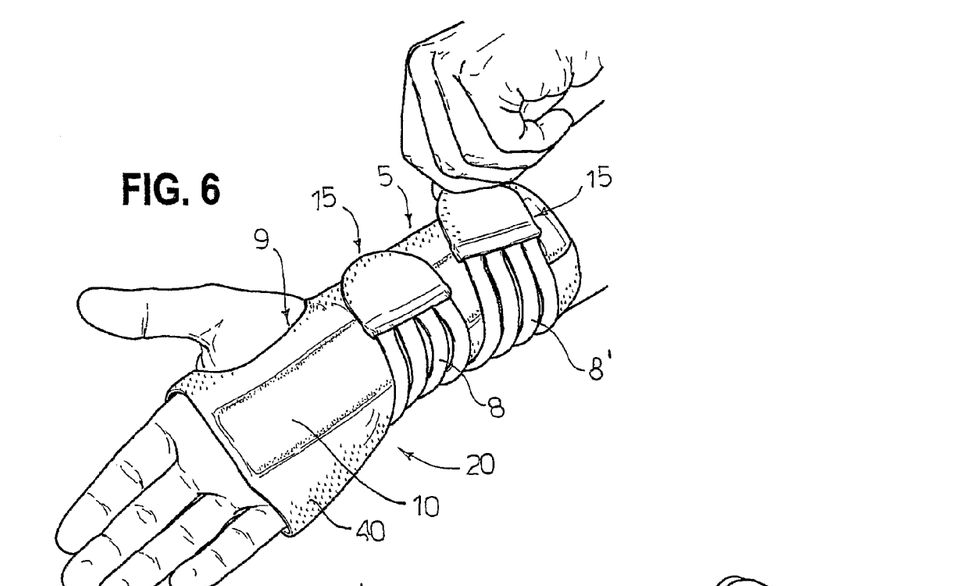
FIGS. 6-8 are three perspective views illustrating the wrist splint of FIG. 5 in the stages of application and removal from the wearer's wrist.
Figures 7, 8:
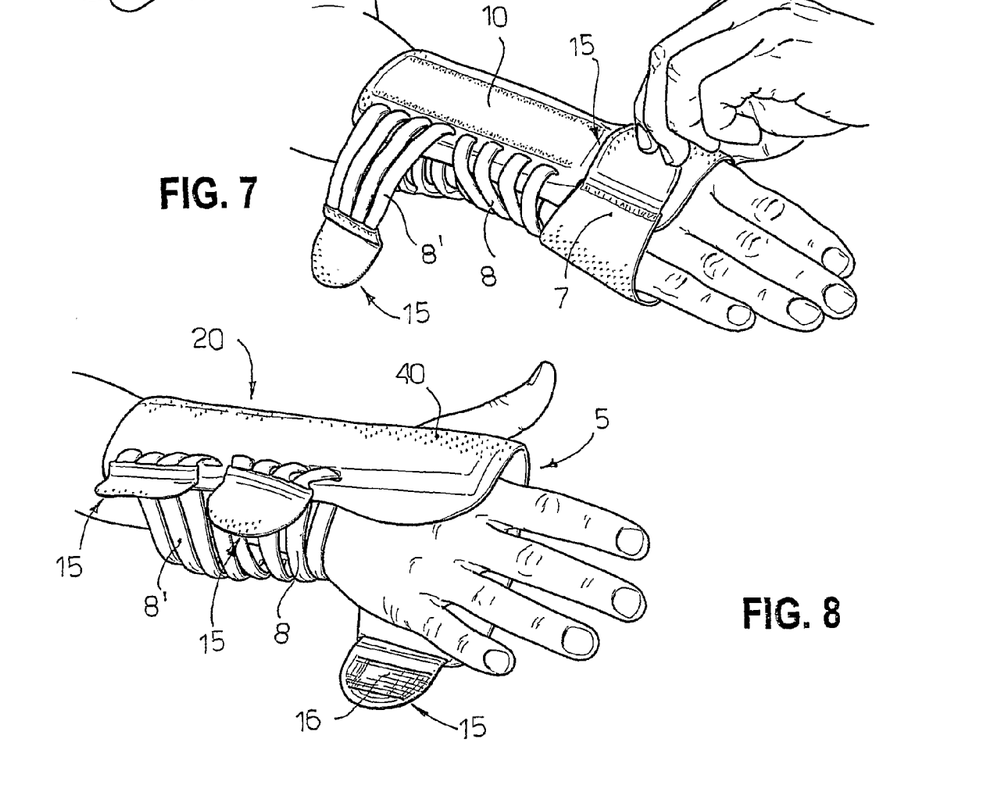

As shown in FIGS. 6, 7 and 8, the splint 20 is fitted on the wrist of the wearer so that the thumb of the hand enters the slot 9 of the splint. Subsequently, the wearer, with the other hand, grips the first fastening element 15 so as to tighten the group of four longer laces 8' as much as possible and thus block the fastening element 15 on the upper surface 40 of the strap 5; then the second fastening element 15 is gripped so as to tighten the group of four shorter laces 8 as much as possible and thus block the fastening element 15 on the upper surface 40 of the strap 5; and lastly the third fastening element 15 is gripped so as to tighten the side band 7 as much as possible and thus block the fastening element 15 on the upper surface 40 of the strap 5.

To remove the splint 20, the wearer disengages the fastening elements 15 and loosens the laces 8, 8' to remove the splint 20 from the wrist.

It should be noted that during application of the splint 20, the undersurface of the laces 8, 8' can come into contact with the wearer's skin. This is not a problem since the undersurface of the laces is made of the same anallergic material as the undersurface of the strap 5.

Furthermore, it should be noted that during application of the splint 20, it can happen, depending upon the size of the wearer's wrist, that the position of the fastening elements 15 coincides with the laces 8, 8' when the laces are perfectly tightened. This situation too does not prove to be a problem since the tipper surface of the laces is made of the same material suitable for Velcro-type fastening as the upper surface of the strap 5. Therefore the fastening elements 15 can be fixed on the laces 8. 8'.

Figure 9:
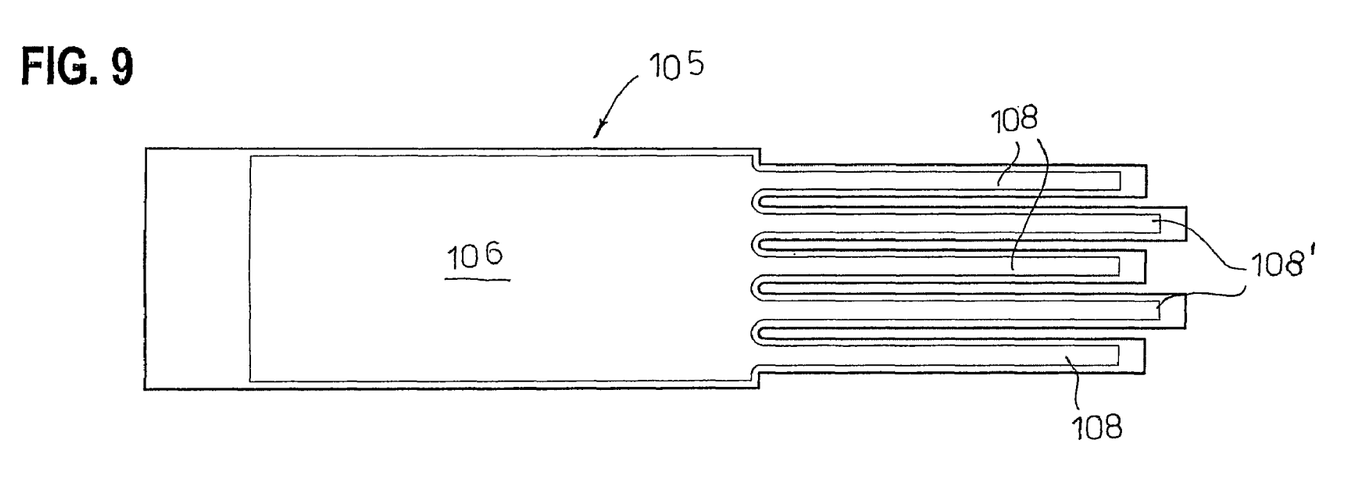
FIGS. 9-11 are three plan views illustrating a spread-out strap during three successive stages of production of a product according to a second embodiment of the invention which provides a wrist support.
Figure 10:
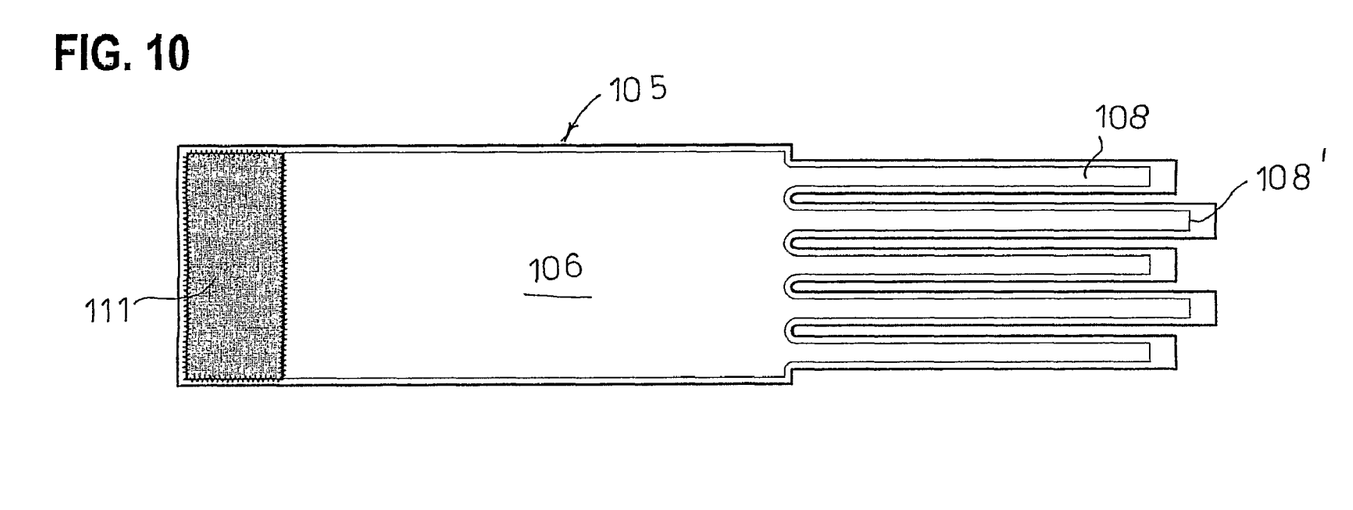
Figures 11, 12:
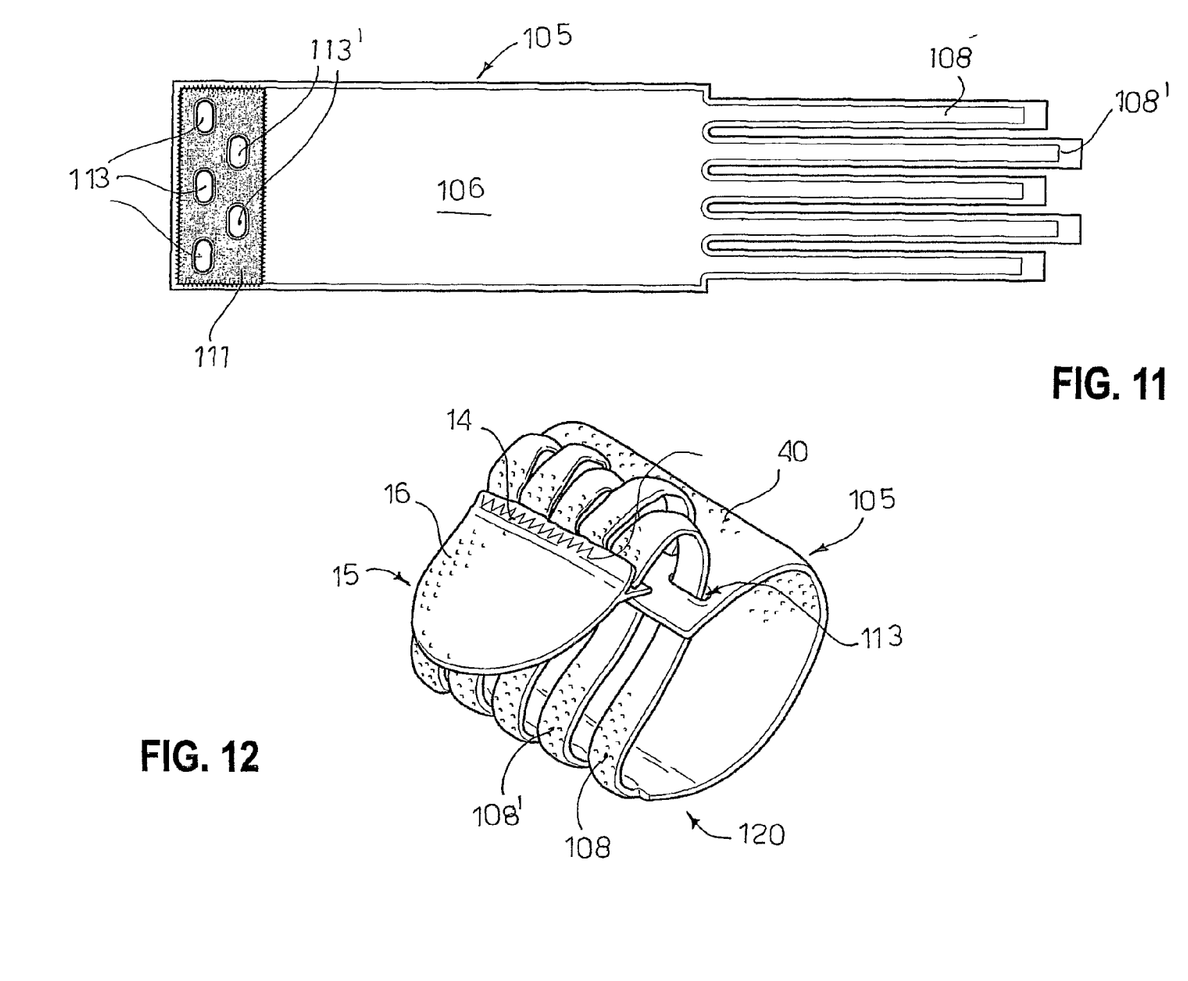
FIG. 12 is a perspective view illustrating the final stage of production of the wrist support according to the invention.

Another product according to a second embodiment of the invention, which provides a wrist brace, illustrated as a whole in FIG. 12 and indicated with reference numeral 120, is described with the aid of FIGS. 9-15.

Production of the wrist brace 120 again starts from a multilayer sheet 1, illustrated in FIG. 1. This sheet is fed toward a die-punching and moulding machine to be die-punched and moulded along its peripheral edge so as to obtain a strap 105 having the shape illustrated in FIG. 9. The strap 105 comprises a substantially rectangular main portion 106 destined to surround the wearer's wrist.

A plurality of laces 108, 108' in the form of rectangular strips protrude from one side of the main portion. To be precise, five laces are provided: three shorter laces 108 alternating with two longer laces 108'.

As shown in FIG. 10, a reinforcing strip 111 disposed near the opposite side to that in which the laces 108, 108' is sewn onto the main portion 106 of the strap 105.

As shown in FIG. 11, coinciding with the reinforcing strip 111, a plurality of eyelets 113, 113' are made, by die-punching, coinciding with the laces 108, 108' and able to accommodate said laces. To be precise, three eyelets 113 are aligned near the opposite side to the laces and another three eyelets 113' are aligned slightly more towards the inside with respect to the three eyelets 113. In this manner the shorter laces 108 engage in the outermost eyelets 113; the longer laces 108', on the other hand, engage in the innermost eyelets 113'.

As shown in FIG. 12, after the laces 108, 108' have been passed through the respective eyelets 113, 113' a Velcro-type fastening element 15 is fixed, by means of sewing 14, to the free ends of the laces 108, 108'. The fastening element 15 is substantially similar to that described in the first embodiment and has on one surface a plurality of hooks 16 able to engage, in a fastening relationship, with the loops 40 provided on the upper surface of the strap 105.

Figure 13:
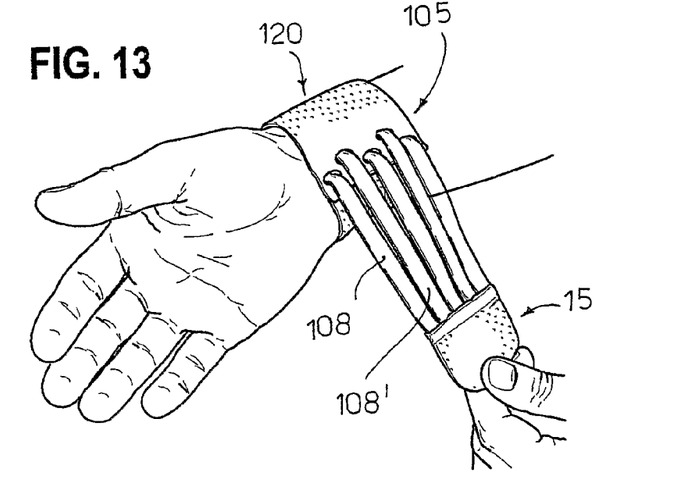
FIGS. 13-15 are three perspective views illustrating the wrist support of FIG. 12 in the stages of application to a wearer's wrist.
Figure 14:
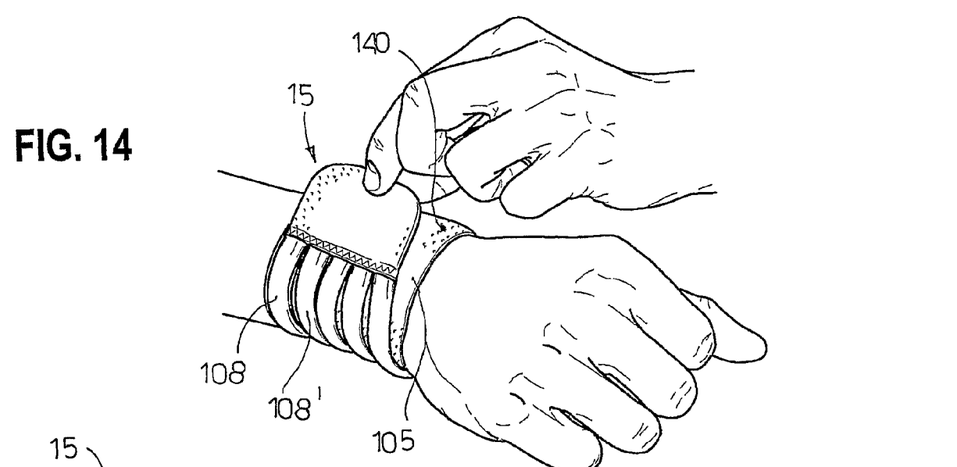
Figure 15:
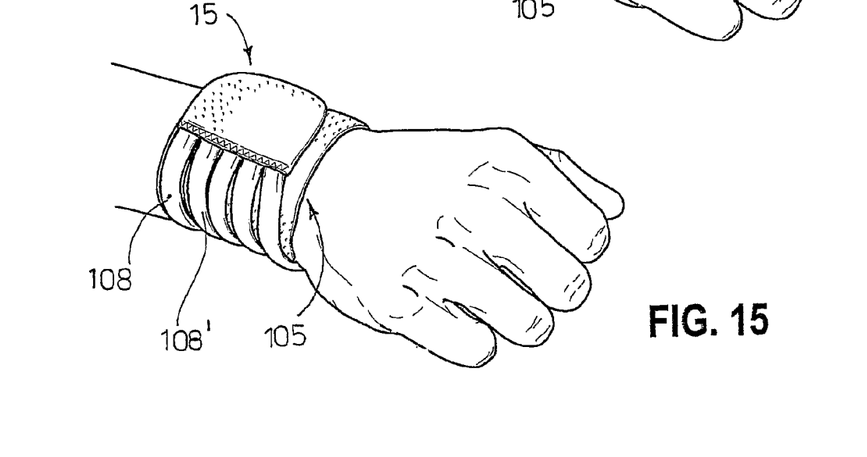

With reference to FIGS. 13, 14 e 15, application of the wrist support 120 on the wearer's wrist is extremely simple. In fact the wearer grips the fastening element 15 with the other hand and pulls the laces 108, 108' to tighten the strap 105 around the wrist. Then the fastening element 15 is applied to the upper surface of the strap 105 so that the hooks 16 of the fastening element engage with the loops 40 of the upper layer 4 of the strap 105. In this manner the wrist brace 120 is in the closed, tightened position and any loosening thereof is avoided.

Figure 16:
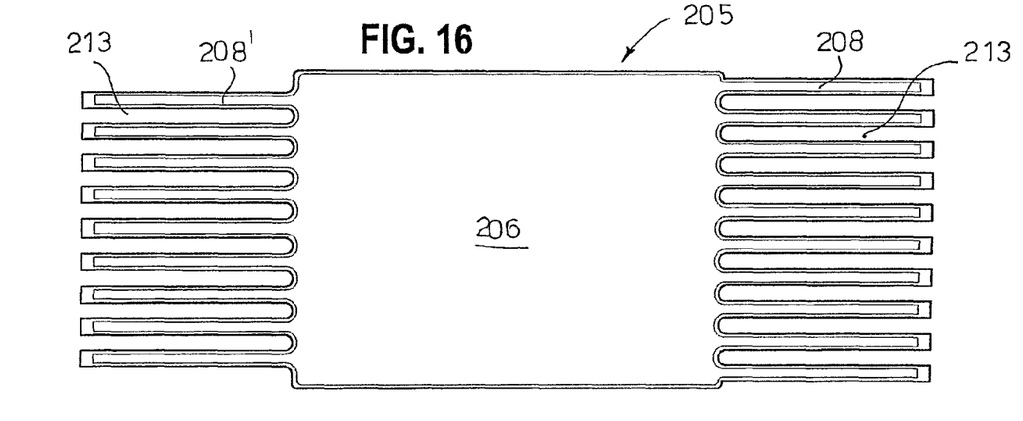
FIG. 16 is a top plan view illustrating a spread-out strap for realization of a portion of knee support according to a third embodiment of the invention.
Figure 17:
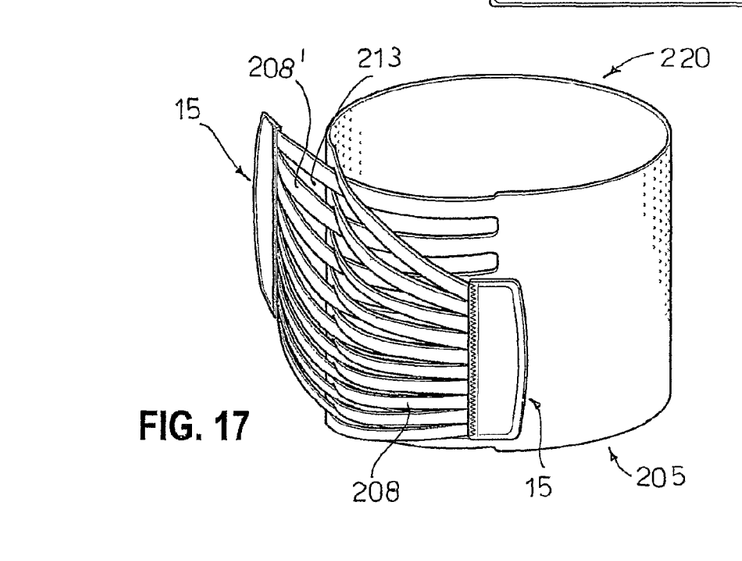
FIG. 17 is a perspective view illustrating the portion of knee support obtained with the strap of FIG. 16, disposed in an open position.
Figure 18:
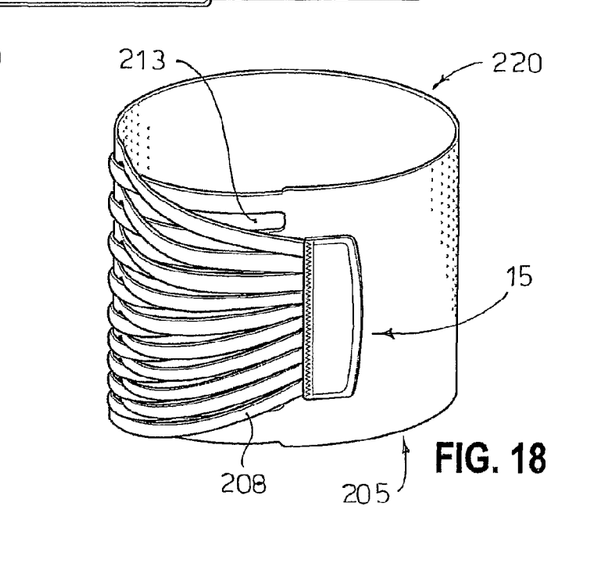
FIG. 18 is a perspective view illustrating the portion of knee support in FIG. 17, in the closed position.

A third embodiment of the invention, which provides a portion of knee brace, illustrated as a whole in FIGS. 17 and 18 and denoted by reference numeral 220, is described with the aid of FIGS. 16-18.

Production of the knee brace 220 again starts from the multilayer sheet 1 illustrated in FIG. 1. This sheet is fed toward a die-punching and moulding machine to be die-punched and moulded along its peripheral edge so as to obtain a strap 205 having the shape illustrated in FIG. 16. The strap 205 comprises a substantially rectangular portion 206 destined to surround a part of the wearer's knee.

A plurality of laces 208, 208' in the form of rectangular strips having the same length and the same width protrude from two opposite sides of the central portion 206. To be exact, with reference to FIG. 16, ten laces 208 which protrude toward the right and nine laces 208' which protrude toward the left are provided. The right and left laces 208, 208' are of the same length and disposed offset from each other, so that a space 213 having a width equal to the width of the lace is formed between two adjacent laces.

In this manner, as shown in FIG. 17, the right-hand laces 208 are inserted in the spaces 213 defined between the left-hand laces 208', whilst the left-hand laces 208' are inserted in the spaces 213 defined between right-hand laces 208. Subsequently two fastening elements 15 of the Velcro type, substantially similar to those described previously, are fixed to the free end of the right-hand laces 208, and left-hand laces 208'.

It should be noted that in this embodiment, it is not necessary to perform any die-punching to obtain the eyelets for passage of the laces.

To tighten the strap 205 around the knee, it is necessary to pull the two fastening elements 15 and then apply them to the upper surface of the strap 205 to fix them in position, as shown in FIG. 18.

Figure 19:
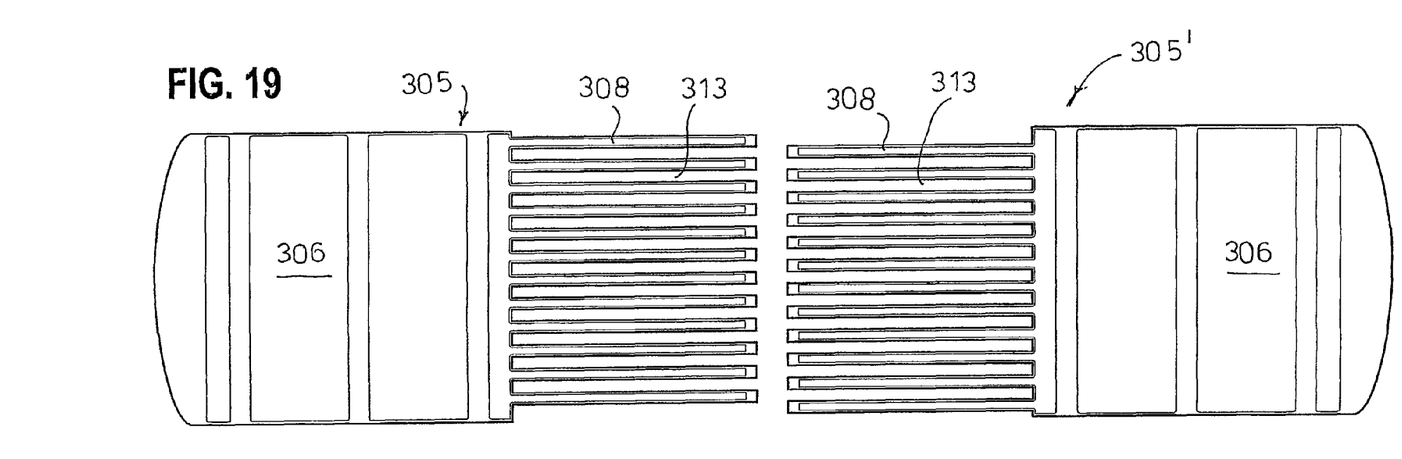
FIGS. 19 and 20 are top plan views illustrating respectively two spread-out straps during two stages of production of a corset according to a fourth embodiment of the invention.
Figure 20:
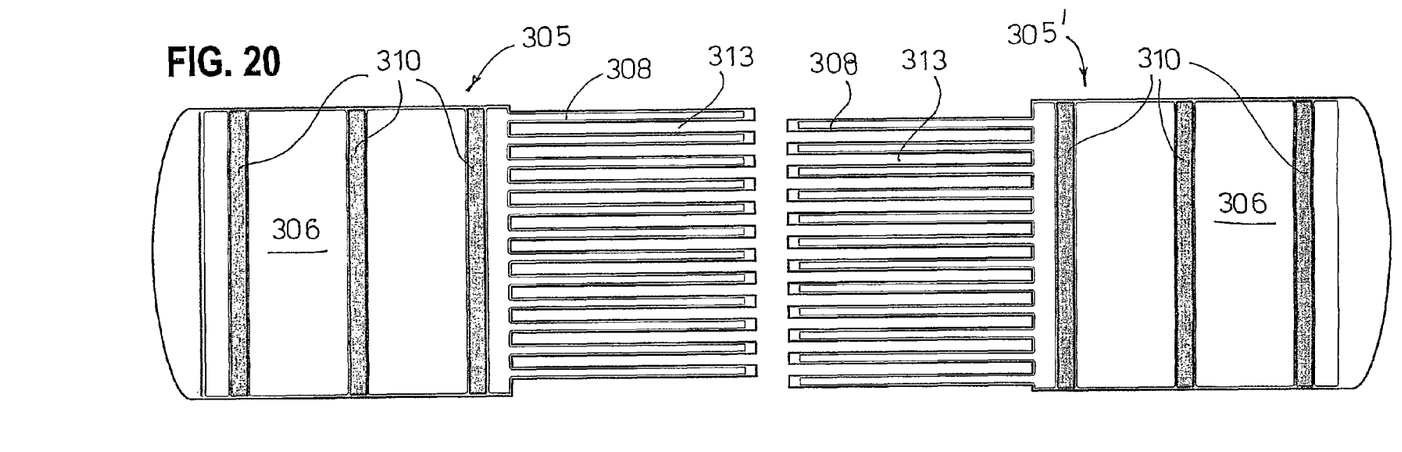
Figure 21:
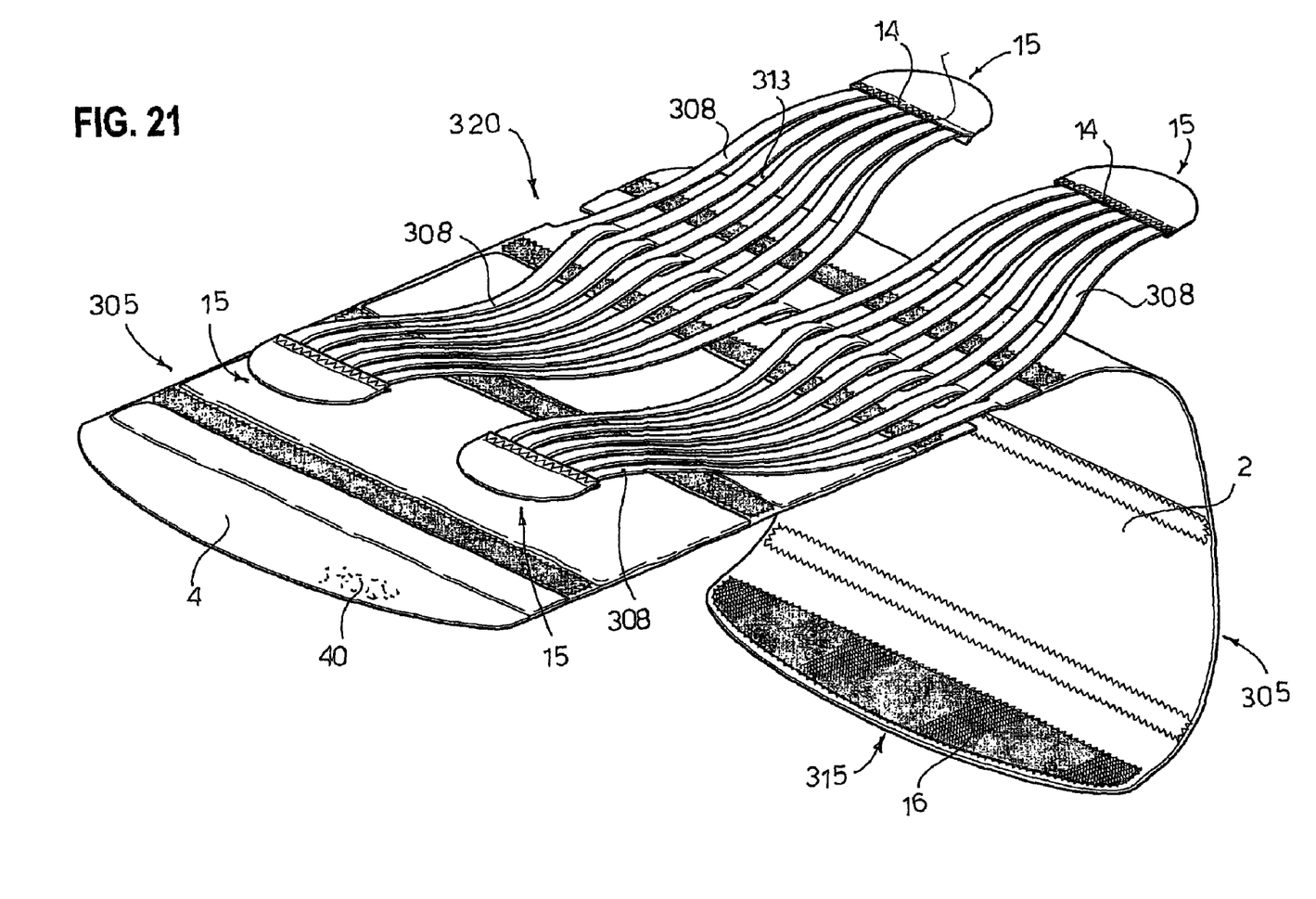
FIG. 21 is a perspective view illustrating a corset obtained with the straps of FIGS. 19 and 20.

A fourth embodiment of the invention which provides for a corset, illustrated as a whole in FIG. 21 and denoted with reference numeral 320, is described with the aid of FIGS. 19-21.

Production of the corset 320 again starts from the multilayer sheet 1 illustrated in FIG. 1. This sheet is fed toward a die-punching and moulding machine to be die-punched and moulded along its peripheral edge so as to obtain two straps 205, 305', substantially the same, having the shapes illustrated in FIG. 19. Each strap 205, 305 comprises a substantially rectangular central portion 306.

A plurality of laces 308 in the form of rectangular strips having the same length and the same width, disposed equidistant from each other so as to define a plurality of spaces 313 of such a width as to receive the laces 308, protrude from one side of the central portion 306. To be precise, ten laces 208 are provide on each surface 305, 305'.

In this case, for reasons of economy, cold die cutting rather than hot moulding or ultrasound moulding of the peripheral edge of the multilayer sheet 1 proves particularly advantageous.

As shown in FIG. 20, in a subsequent step reinforcing strips 310 are sewn onto the top surface of each strap 305, 305'.

As shown in FIG. 21, the laces 308 of a strap are inserted into the spaces 313 of the other strap 305'. Subsequently, four fastening elements 15 of the Velcro type, substantially similar to those previously described, are fixed to the ends of the four groups of five laces 308.

Lastly, in the bottom layer 2 of a strap 305', near to the side opposite that of the laces 308, a strip 315 of a Velcro-type fastening element, which provides a plurality of hooks 16 able to couple with the loops 40 provided on the outer surface of the top layer 4 of the strap 205, is applied by sewing.

Numerous variations and changes of detail within the reach of a person skilled in the art can be made to the present embodiments of the invention without thereby departing from the scope of the invention as set forth in the appended claims.

The invention claimed is:

1. A medical product or sports product for bracing joints, comprising:
 a main strap configured to surround a part of the body to be supported, said main strap including a bottom-most layer configured to come into contact with a wearer's skin, an intermediate layer of padding over said bottom-most layer, and a top layer over said intermediate layer and configured to face outward, said layers of the main strap are coupled to each other and a peripheral edge of the main strap is die punched;
 a plurality of strips or laces extending from said peripheral edge as a unitary one-piece extension of said main strap, said plurality of strips or laces have an under surface of an anallergic material configured to contact a wearer's skin and have a top surface of a material configured to enable hook and loop fastening;
 a plurality of eyelets configured to receive said laces are formed in said main strap; and
 a slot configured to allow the passage of a thumb of a hand is formed in said main strap, an edge of said slot being moulded,
 wherein at ends of said plurality of strips or laces there is at least one hook and loop fastening element configured to be fixed to an upper-most surface of said top layer of the main strap.

2. The product according to claim 1, wherein said bottom-most layer is made of anallergic material, said intermediate layer of padding is made of soft, breathable material, and said upper layer is made of a material configured to allow hook and loop fastening.

3. The product according to claim 2, wherein said bottom-most layer is made of cotton fabric, said intermediate layer of padding is made of open-cell foamed plastic material, and said top layer is made of nylon treated to have an upper surface suitable for hook and loop fastening.

4. The product according to claim 3, wherein said intermediate layer of padding is polyurethane.

5. The product according to claim 1, wherein the peripheral edge of said strap is at least one of pressure moulded, heat welded and ultrasound welded.

6. The product according to claim 1, wherein said eyelets are formed in a reinforcing strip sewn onto the upper-most surface of said main strap.

7. A medical product or sports product for bracing joints, comprising: a main strap configured to surround a part of the body to be supported, said main strap including a bottom-most layer configured to come into contact with a wearer's skin, an intermediate layer of padding over said bottom-most layer, and a top layer over said intermediate layer and configured to face outward, said layers of the main strap are coupled to each other and peripheral sides of the main strap are die punched; and a plurality of strips or laces extending from said peripheral sides as a unitary one-piece extension of said main strap, said plurality of strips or laces have an under surface of an anallergic material configured to contact a wearer's skin and have a top surface of a material configured to enable hook and loop fastening, wherein at ends of said plurality of strips or laces there is at least one hook and loop fastening element configured to be fixed to an upper-most surface of said top layer of the main strap, and wherein said strips or laces are disposed in two opposite sides of said main strap and are spaced apart from each other so as to form spaces configured to allow the passage of laces, so that the laces of one side engage in the spaces of the laces of the other side and vice versa, said laces being inwardly spaced from respective upper and lower edges of said main strap.

8. A medical product or sports product for bracing joints, comprising:
 two main straps configured to surround a part of the body to be supported, each of said two main straps including a bottom-most layer configured to come into contact with a wearer's skin, an intermediate layer of padding over said bottom-most layer, and a top layer over said intermediate layer and configured to face outward, said layers of each respective said two main straps are coupled to each other and a peripheral edge of each of the two main straps is die punched; and
 a plurality of laces extending from said peripheral edge at one respective side of each of said two main straps as a unitary one-piece extension of a corresponding one of said two main straps, said plurality of laces are configured to cross over each other and have an under surface of an anallergic material configured to contact a wearer's skin and have a top surface of a material configured to enable hook and loop fastening,
 wherein at ends of said plurality of laces there is at least one hook and loop fastening element configured to be fixed to an upper-most surface of said top layer of one of the two main straps, and
 wherein another hook and loop fastening element configured to engage on the upper-most surface of the first one of said two main straps is sewn on an undersurface of a second one of said two main straps.

9. A medical product or sports product for bracing joints, comprising:
 a main strap configured to surround a part of the body to be supported, said main strap including a bottom-most layer configured to come into contact with a wearer's skin, an intermediate layer of padding over said bottom-most layer, and a top layer over said intermediate layer and configured to face outward, said layers of the main strap are coupled to each other and a peripheral edge of the main strap is die punched;
 a plurality of strips or laces extending from said peripheral edge as a unitary one-piece extension of said main strap, said plurality of strips or laces have an under surface of an anallergic material configured to contact a wearer's skin and have a top surface of a material configured to enable hook and loop fastening;

a plurality of eyelets configured to receive said laces are formed in said main strap; and pockets configured to accommodate metal stiffening plates are sewn on an upper surface of said main strap, wherein at ends of said plurality of strips or laces there is at least one hook and loop fastening element configured to be fixed to an upper-most surface of said top layer of the main strap.

10. A medical product or sports product for bracing joints, comprising:

a main strap configured to surround a part of the body to be supported, said main strap including a bottom-most layer configured to come into contact with a wearer's skin, an intermediate layer of padding over said bottom-most layer, and a top layer over said intermediate layer and configured to face outward, said layers of the main strap are coupled to each other and a peripheral edge of the main strap is die punched;

a plurality of strips or laces extending from said peripheral edge as a unitary one-piece extension of said main strap, said plurality of strips or laces have an under surface of an anallergic material configured to contact a wearer's skin and have a top surface of a material configured to enable hook and loop fastening;

a plurality of eyelets configured to receive said laces are formed in said main strap; and a band that is a unitary, one-piece extension of said main strap and extending in a same direction from said peripheral edge as said plurality of laces, said band having a width that is wider than that of said plurality of laces and a length that is less than that of said plurality of laces, wherein at ends of said plurality of strips or laces there is at least one hook and loop fastening element configured to be fixed to an upper-most surface of said top layer of the main strap.

* * * * *